(12) United States Patent
Watson

(10) Patent No.: US 8,986,753 B2
(45) Date of Patent: Mar. 24, 2015

(54) WEIGHT LOSS COMPOSITIONS AND METHODS FOR APPETITE SUPPRESSION

(71) Applicant: Matthew Watson, Redondo Beach, CA (US)

(72) Inventor: Matthew Watson, Redondo Beach, CA (US)

(*) Notice: Subject to any disclaimer, the term of this patent is extended or adjusted under 35 U.S.C. 154(b) by 0 days.

(21) Appl. No.: 14/291,808

(22) Filed: May 30, 2014

(65) Prior Publication Data
US 2014/0370095 A1 Dec. 18, 2014

Related U.S. Application Data

(60) Provisional application No. 61/836,129, filed on Jun. 17, 2013.

(51) Int. Cl.

| | |
|---|---|
| A01N 65/00 | (2009.01) |
| A61K 36/81 | (2006.01) |
| A61K 36/67 | (2006.01) |
| A61K 36/9068 | (2006.01) |
| A61K 36/54 | (2006.01) |
| A61K 36/31 | (2006.01) |
| A61K 36/28 | (2006.01) |
| A61K 31/51 | (2006.01) |
| A61K 31/525 | (2006.01) |
| A61K 31/455 | (2006.01) |
| A61K 31/197 | (2006.01) |
| A61K 31/714 | (2006.01) |
| A23L 1/29 | (2006.01) |
| A23L 2/02 | (2006.01) |
| A23L 2/52 | (2006.01) |
| A23L 1/302 | (2006.01) |

(52) U.S. Cl.
CPC .............. *A61K 36/81* (2013.01); *A61K 36/67* (2013.01); *A61K 36/9068* (2013.01); *A61K 36/54* (2013.01); *A61K 36/31* (2013.01); *A61K 36/28* (2013.01); *A61K 31/51* (2013.01); *A61K 31/525* (2013.01); *A61K 31/455* (2013.01); *A61K 31/197* (2013.01); *A61K 31/714* (2013.01); *A23L 1/293* (2013.01); *A23L 2/02* (2013.01); *A23L 2/52* (2013.01); *A23L 1/302* (2013.01); *A23V 2002/00* (2013.01)
USPC .......................................................... 424/725

(58) Field of Classification Search
None
See application file for complete search history.

(56) References Cited

U.S. PATENT DOCUMENTS 8,323,682 B2   12/2012   Cherkassky

FOREIGN PATENT DOCUMENTS

| WO | 2004/032950 | 4/2004 |
| WO | 2007/106968 | 9/2007 |

*Primary Examiner* — Michael Meller
(74) *Attorney, Agent, or Firm* — Milton L. Honig

(57) ABSTRACT

A beverage composition for weight loss is provided which includes cayenne pepper; a palate enhancing agent selected from the group consisting of fruits, herbs, vegetables and mixtures thereof, the agent including pulp of the fruits, the herbs, the vegetables or the mixtures thereof; a least two spices selected from the group consisting of black or white pepper, ginger, cinnamon, mustard seed and mixtures thereof; and water in an amount from 80 to 99% by weight of the composition; and wherein the composition has a total calorie content from 0 to 100 based on 100 gram of the composition.

10 Claims, No Drawings

WEIGHT LOSS COMPOSITIONS AND METHODS FOR APPETITE SUPPRESSION

BACKGROUND OF THE INVENTION

1. Field of the Invention

The invention concerns weight loss compositions and methods for appetite suppression, particularly compositions which taste well.

2. The Related Art

Numerous humans suffer from a condition of being overweight. In many instances the overweight condition is at a level of obesity. Medical problems are associated with increased weight. Amongst the potential health issues are cancers, diabetes, joint problems and heart diseases.

There are also social implications. People who substantially exceed recognized weight limits often have a poor opinion of themselves. This may even lead to depression. Society also extracts a price. Today slim is attractive. Fat persons are perceived as unattractive and thereby are socially less accepted. Sexual and other personal relationships prove difficult when a person is overweight. There also are economic reverberations to being fat. Potential employers are hesitant to hire these people. There may be the fear, albeit unjustifiable, that overweight persons are slothful and unenergetic.

Fortunately, there are methods to slim down. Prominent are the celebrated diet concepts. Some have found success in low carbohydrate regimes; others have turned to protein diets; and still others have embraced meal replacements. Another approach has been group therapy type plans such as WEIGHT WATCHERS™.

Taste and flavor are important to satiety. Any diet must also take into consideration taste and flavor.

Amongst patent disclosures suggesting solutions to the excess weight problem are the following.

U.S. Pat. No. 8,323,682 B2 (Cherkassky) reports appetite suppression with compositions that contain a cellulose product, a stimulant (e.g. caffeine), spice (cayenne pepper), salt and a sweetener all formed into a paste.

WO 2007/106968 A1 (Heuer) discloses compositions for increasing a person's metabolic rate. The compositions contain dandelion root extract, n-acetyl-1-tyrosine, *gynostemma pentaphyllum* and picamilone. Optionally present are various plant extracts and even cayenne pepper powder.

WO 2004/032950 A1 (Muller) describes compositions to promote weight loss wherein the appetite suppressant is either L-tyrosine or *garcinia cambogia*. Further components may include a thermogenic agent such as cayenne pepper. Other possible ingredients are cinnamon, copper Coenzyme Q, *ginko biloba*, ginseng, *gymnema sylvestre*, manganese, pantothenic acid, vanadium, vanadyl sulfate, vitamin C, vitamin E, niacin and zinc.

A problem with the known art is that many good tasting weight loss foods are ineffective while many effective ones are unpalatable. A need is evident for good tasting weight loss effective foods.

SUMMARY OF THE INVENTION

A beverage composition for weight loss is provided which includes:
(i) cayenne pepper;
(ii) a palate enhancing agent selected from the group consisting of fruits, herbs, vegetables and mixtures thereof, the agent including pulp of the fruits, the herbs, the vegetables or the mixtures thereof;
(iii) at least two spices selected from the group consisting of black or white pepper, ginger, cinnamon, mustard seed and mixtures thereof;
(iv) water in an amount from 80 to 99% by weight of the composition; and wherein the composition has a total calorie content from 0 to 100 based on 100 gram of the composition.

DETAILED DESCRIPTION OF THE INVENTION

Now it has been found that a combination of cayenne pepper and at least two other spices formulated in 80 to 99% water is effective to achieve significant weight loss when consumed over an extended period of time. Furthermore, the composition overcomes the normally irritating taste of cayenne pepper and the other spices by being present in a cocktail of real fruits and/or vegetables and/or herbs.

A first component of the herein described compositions is cayenne pepper. Alternate names of this component are Guinea spice or cow-horn or red pepper. It is red colored when allowed to ripen to maturity. Named for the city of Cayenne in French Guiana, it is a cultivar of *capsicum annuum* related to bell peppers, jalapenos, paprika and others. The *capsicum* genus is in the nightshade family (Solanaceae). Amounts of cayenne pepper in the composition may range from about 0.00001 to about 0.01, preferably from about 0.00005 to about 0.002, more preferably from about 0.0001 to about 0.001, and optimally from 0.00015 to 0.0003% by weight of the composition.

A second component of the herein described compositions is a palate enhancing agent selected from fruits, herbs, vegetables or combinations therefor. The palate enhancing agent will include the pulp of the respective fruits, herbs or vegetables. In other words, palate enhancing agent is meant to exclude fruit, herb or vegetable extracts or juices; these do not contain original pulp. In certain embodiments, the compositions may contain fruit, herb or vegetable extracts or juices in addition to the palate enhancing agent. Amounts of the palate enhancing agent may be present from about 0.0001 to about 50, preferably from about 0.001 to about 35, more preferably from about 0.03 to about 30, and optimally 0.05 to 25% by weight of the composition.

Typical palate enhancing agents are fruits selected from the group consisting of pineapple, raspberries, strawberries, blueberries, cranberries, mango, peach, apple, orange, pear, apricot, plum, guava, papaya, grapefruit, lemon, blackberries, pomegranate, honeydew, coconut, kiwi, apple, nectar, grape, hawthorn fruit, goji berry, dragon fruit, cherry and banana. Vegetables useful as palate enhancing agents include avocado, carrot, beet, tomato, celery, spinach, sprouts, asparagus, beans and cucumbers. Herbs useful as palate enhancing agents include mint, and bilberry. Most preferred is fruit. One particular combination is raspberries and pineapple in a weight ratio ranging from about 1:20 to about 20:1, preferably from about 1:10 to about 10:1, optimally from about 1:2 to about 1:5.

A further component of the herein compositions are at least two spices. These may be selected from the group consisting of black or white pepper, ginger, cinnamon, mustard seed and mixtures thereof. Amounts of each spice in the at least two spice grouping in the composition may range from about 0.00001 to about 0.01, preferably from about 0.00005 to about 0.002, more preferably from about 0.0002 to about 0.001, and optimally from 0.00015 to 0.0003% by weight of the composition. Of particular usefulness are the presence of each of black or white pepper, ginger, cinnamon, and mustard seed.

Particle sizes of the cayenne pepper and of the spices (black/white pepper, ginger, cinnamon, mustard seed) may have importance for inducing a long-lived energy level feeling by the consumer. By adjusting particle size, taste may also achieve greater consistency and avoid some spices from overwhelming the overall composition flavor. Typical particle sizes are those which can pass through sieve openings of sieves ranging from US Mesh 20 (<0.841 mm) down to US Mesh 270 (<0.053 mm), with US Mesh sizes 70 to 150 being most useful. Thus, the general range of particle sizes may range from 0.050 to 0.900 mm, sometimes from 0.080 to 0.250 mm, and sometimes from 0.149 to 0.210 mm.

Water will be present in the herein compositions in amounts ranging from about 80 to 99, preferably from about 90 to 98, and optimally from 95 to 97.5% by weight of the composition. The aforementioned water concentrations are meant to encompass total water content of the composition regardless of source. For instance, any water content brought in via the palate enhancing agent is a weight attributed to be within the water content described in this paragraph.

Water present in the composition may advantageously be added as a sterilized or pasteurized liquid or can be heat treated or irradiated after having been mixed with other components of the composition. In sterilized form, no pathogenic microbes (*Salmonella, Listeria, Escherichia coli, Staphylococcus aureus, Yerina,* and/or *Campylobacter*) will be present. Alternatively, pasteurized water may be employed which insures that the water and composition are essentially free of the pathogenic microbes.

Advantageously present in the herein compositions will be milk thistle extract, the extract being obtained from seeds of the milk thistle. Amounts may range from about 0.000001 to about 0.001, preferably from about 0.00001 to about 0.0001, and more preferably from 0.00003 to 0.00008% by weight of the composition.

Advantageously, vitamins may be present in the compositions. Of particular note are the vitamin B type including $B_1$, $B_2$, $B_3$ (niacinamide), $B_5$, $B_6$ and $B_{12}$. In one embodiment, all of the six aforementioned vitamin B types are incorporated into the composition. Amounts of each of the vitamin B types may range from about 0.000001 to about 0.001, preferably from about 0.00001 to about 0.0001, and more preferably from 0.00003 to 0.0001% by weight of the composition.

Although in some embodiments of this invention caffeine may be present, it has been found advantageous to formulate compositions without caffeine and thereby avoid reported undesirable affects. Thus amounts of caffeine may be limited to a maximum range from 0.000001 to 0.5, and in some instances from 0.00001 to 0.0001% by weight of the composition, but especially be entirely absent.

Calorie content of compositions of this invention may range from 0 to 100, possibly 0 to 50, preferably from 10 to 40, and usually from 20 to 30 calories per 100 gram of composition.

A variety of optional ingredients may be present in the compositions. In certain embodiments, the compositions may contain edible polyols such as sorbitol, xylitol, mannitol, polyethylene glycols, polypropylene glycols, co-polymers of ethylene and propylene glycol (e.g. Poloxamers®) and combinations thereof. Artificial sweeteners may be present in some embodiments but are usually not formulated into the preferred formulas. These sweeteners may include aspartame, Sucralose®, acesulfame, saccharine, stevia and combinations thereof including potassium and sodium salts of these where appropriate.

Other optional ingredients are acidulants, colorants, preservatives and emulsifiers, each in amounts to perform their functional effects. Illustrative acidulants include potassium or sodium salts of citric, tartaric, ascorbic, phosphonic and phosphoric acids. Often they can serve the dual function as a preservative. Other common preservatives are ethylenediaminetetraacetic acid salts, benzoate salts and sorbate salts. Illustrative colorants include FD&C Yellow No. 5, Blue No. 1, Blue No. 2, Red No. 40 and combinations. Emulsifiers are useful where the compositions contain oily ingredients in the water carrier. Typical emulsifiers are glycerol monostearate, polyoxyethylenesorbate and sodium polyoxyethylene stearate.

Compositions described herein may be packaged in single serve containers, either plastic bottles, metal cans, glass bottles or cellulosic packs. The containers are appropriately sterilized prior to introduction of the compositions.

Example 1

An illustrative formula is set forth in the Table below.

| Ingredient | Weight % |
|---|---|
| Component A: | |
| Cayenne Pepper | 0.00026 (⅛ tsp.) |
| Black Pepper | 0.00026 (⅛ tsp.) |
| Ginger | 0.00026 (⅛ tsp.) |
| Cinnamon | 0.00026 (⅛ tsp.) |
| Mustard Seed | 0.00026 (⅛ tsp.) |
| Component B: | |
| Vitamin $B_1$ | 0.00004 (100 mg) |
| Vitamin $B_2$ | 0.00004 (100 mg) |
| Vitamin $B_3$ | 0.00020 (500 mg) |
| Vitamin $B_5$ | 0.00010 (250 mg) |
| Vitamin $B_6$ | 0.00004 (100 mg) |
| Vitamin $B_{12}$ | <0.00001 (500 mcg) |
| Milk Thistle | 0.00006 (140 mg) |
| Component C: | |
| Crushed Pineapple | 0.2156 (18 ounces) |
| Crushed Raspberry | 0.0676 (160 grams) |
| Component D: | |
| Water | to 100 (10 cups = 2366 gm) |

The composition of this Example was prepared by mixing Component B with 237 grams (1 cup) of water to form a first mixture. Separately, Component C was mixed with 237 grams (1 cup) of water to form a second mixture. Component A was then dosed into Component D constituting 1900 grams (8 cups) water forming a main mixture. The first and second mixtures were then added to the main mixture. The resultant liquid formula was then blended together till homogeneous. Calorie content was analyzed to be 30 calories per 8 liquid ounces of the resultant liquid formula.

Example 2

A series of compositions were prepared to evaluate various physical properties, including taste, of formula variants. For the solid particulate ingredients, 60% of the particulates will pass through the designated (US Mesh) sieve screen. A first test formula is set forth in the Table below.

| Ingredient | Weight (grams/solids) or, Volume (oz./liquids) |
|---|---|
| Component A: | |
| Cayenne Pepper | 1.00 gram (US Mesh 60) |
| Black Pepper | 1.20 gram (US Mesh 60) |
| Ginger | 1.25 gram (US Mesh 70) |
| Cinnamon | 2.00 gram (US Mesh 70) |
| Mustard Seed | 2.00 gram (US Mesh 70) |

-continued

| Ingredient | Weight (grams/solids) or, Volume (oz./liquids) | |
|---|---|---|
| Component B: | | |
| Vitamin $B_1$ | 100 | mg |
| Vitamin $B_2$ | 100 | mg |
| Vitamin $B_5$ | 250 | mg |
| Vitamin $B_6$ | 100 | mg |
| Vitamin $B_{12}$ | 500 | mcg |
| Niacinamide | 500 | mg |
| Milk Thistle | 145 | mg |
| Component C: | | |
| Crushed Pineapple | 18 | ounces |
| Crushed Raspberry | 10 | ounces |
| Component D: | | |
| Water | 80 | ounces |

The composition of this Example was prepared in a manner similar to the process described under Example 1. The resultant liquid formula is measured for calorie content to be no higher than 80 calories per 8 liquid ounces.

Example 3

A second test formula of the aforementioned series of compositions was prepared to evaluate various physical properties, including taste. Ingredients of the second test formula are set forth in the Table below.

| Ingredient | Weight (grams/solids) or Volume (oz./liquids) | |
|---|---|---|
| Component A: | | |
| Cayenne Pepper | 1.50 | gram (US Mesh 60) |
| Black Pepper | 1.50 | gram (US Mesh 60) |
| Ginger | 1.50 | gram (US Mesh 80) |
| Cinnamon | 2.20 | gram (US Mesh 80) |
| Mustard Seed | 2.00 | gram (US Mesh 80) |
| Component B: | | |
| Vitamin $B_1$ | 200 | mg |
| Vitamin $B_2$ | 200 | mg |
| Vitamin $B_5$ | 250 | mg |
| Vitamin $B_6$ | 200 | mg |
| Vitamin $B_{12}$ | 1000 | mcg |
| Niacinamide | 1000 | mg |
| Milk Thistle | 350 | mg |
| Component C: | | |
| Crushed Pineapple | 20 | ounces |
| Crushed Raspberry | 12 | ounces |
| Component D: | | |
| Water | 95 | ounces |

The composition of this Example was prepared in a manner similar to the process described under Example 1. The resultant liquid formula is measured for calorie content to be no higher than 80 calories per 8 liquid ounces.

Example 4

A third test formula of the aforementioned series of compositions was prepared to evaluate various physical properties, including taste. Ingredients of the third test formula are recorded in the Table below.

| Ingredient | Weight (grams/solids) or Volume (oz./liquids) | |
|---|---|---|
| Component A: | | |
| Cayenne Pepper | 1.50 | gram (US Mesh 60) |
| Black Pepper | 1.50 | gram (US Mesh 60) |
| Ginger | 2.00 | gram (US Mesh 100) |
| Cinnamon | 2.20 | gram (US Mesh 100) |
| Mustard Seed | 2.50 | gram (US Mesh 100) |
| Component B | | |
| Vitamin $B_1$ | 200 | mg |
| Vitamin $B_2$ | 200 | mg |
| Vitamin $B_5$ | 250 | mg |
| Vitamin $B_6$ | 200 | mg |
| Vitamin $B_{12}$ | 1000 | mcg |
| Niacinamide | 1000 | mg |
| Milk Thistle | 350 | mg |
| Component C: | | |
| Crushed Pineapple | 22 | ounces |
| Crushed Raspberry | 10 | ounces |
| Component D: | | |
| Water | 90 | ounces |

The composition of this Example was prepared in a manner similar to the process described under Example 1. The resultant liquid formula is measured for calorie content to be no higher than 80 calories per 8 liquid ounces.

Example 5

A fourth test formula of the aforementioned series of compositions was prepared to evaluate various physical properties, including taste. Ingredients of the fourth test formula are recorded in the Table below.

| Ingredient | Weight (grams/solids) or Volume (oz/liquids) | |
|---|---|---|
| Component A: | | |
| Cayenne Pepper | 1.60 | gram (US Mesh 80) |
| Black Pepper | 1.60 | gram (US Mesh 80) |
| Ginger | 2.15 | gram (US Mesh 100) |
| Cinnamon | 2.25 | gram (US Mesh 100) |
| Mustard Seed | 2.50 | gram (US Mesh 100) |
| Component B: | | |
| Vitamin $B_1$ | 200 | mg |
| Vitamin $B_2$ | 200 | mg |
| Vitamin $B_5$ | 250 | mg |
| Vitamin $B_6$ | 300 | mg |
| Vitamin $B_{12}$ | 1000 | mcg |
| Milk Thistle | 350 | mg |
| Component C: | | |
| Crushed Pineapple | 22 | ounces |
| Crushed Raspberry | 10 | ounces |
| Component D: | | |
| Water | 90 | ounces |

The composition of this Example was prepared in a manner similar to the process described under Example 1. The resultant liquid formula is measured to be no higher than 80 calories per 8 liquid ounces.

Example 6

A fifth test formula of the aforementioned series of compositions was prepared to evaluate various physical properties, including taste. Ingredients of the fifth test formula are recorded in the Table below.

| Ingredient | Weight (grams/solids) or Volume (oz./liquids) |
|---|---|
| Component A: | |
| Cayenne Pepper | 1.60 gram (US Mesh 80) |
| Black Pepper | 2.00 gram (US Mesh 100) |
| Ginger | 2.15 gram (US Mesh 100) |
| Cinnamon | 2.25 gram (US Mesh 100) |
| Mustard Seed | 2.50 gram (US Mesh 100) |
| Component B: | |
| Vitamin $B_1$ | 200 mg |
| Vitamin $B_2$ | 200 mg |
| Vitamin $B_5$ | 250 mg |
| Vitamin $B_6$ | 300 mg |
| Vitamin $B_{12}$ | 1000 mcg |
| Milk Thistle | 350 mg |
| Component C: | |
| Crushed Pineapple | 22 ounces |
| Crushed Raspberry | 10 ounces |
| Component D: | |
| Water | 90 ounces |

The composition of this Example was prepared in a manner similar to the process described under Example 1. The resultant liquid formula is measured for calorie content to be no higher than 80 calories per 8 liquid ounces.

Example 7

Panels of tasters evaluated the test formulas outlined in Examples 2-6. There were 18 to 20 people per panel. Among the properties evaluated for each drink were: odor, imparted energy level (i.e. 'jolt'), balance between fruit juices and spices for overall flavor, and visual impact. Results of the panel evaluations are outlined in the Table below.

TABLE

| Example | Preference Rating |
|---|---|
| 2 | 3 |
| 3 | 4 |
| 4 | 4 |
| 5 | 5 |
| 6 | 5 |

Preference Ratings on a 1 to 5 scale (least desirable to best) were given for each of the test formulas. The greatest preference was for the composition detailed under Examples 5 and 6. The smaller particle sizes of the cayenne/black peppers and of the ginger/ground mustard/cinnamon (US Mesh 80 and 100) in Examples 5 and 6 are believed contributory to the improved Preference Rating.

Example 8

Weight loss efficacy was tested on the formula outlined under Example 1. A 20 year old male weighing 259 pounds drank 8 ounces of the formula at breakfast and at dinner time. Within less than one year, the subject male had slimmed to 190 pounds. The final weight was maintained for greater than an additional year with continued regular ingestion of the formula.

Example 9

A 40 year old male weighing 315 pounds drank 8 ounces of the Example 1 formula daily at lunch, and at dinner time. Within less than two months the subject had lost 30 pounds. The subject continues to lose weight with regular ingestion of the formula.

While the invention has been described with reference to specific embodiments, it should be understood that numerous modifications and variations are possible and are to be regarded as within the scope and spirit of this invention.

What is claimed is:

1. A beverage composition for weight loss consisting essentially of:
   (i) cayenne pepper present in an amount from about 0.00001 to about 0.01% by weight of the composition, and wherein the cayenne pepper has a particle size ranging from 0.050 to 0.900 mm;
   (ii) a palate enhancing agent which is a fruit selected from the group consisting of pineapple, raspberry, lemon, grape, blueberry, cherry and mixtures thereof, the agent including pulp of the fruit, the palate enhancing agent being present in an amount from about 0.0001 to about 50% by weight of the composition;
   (iii) at least four spices which are black or white pepper, ginger, cinnamon and mustard seed each present in an amount from about 0.00001 to about 0.01% by weight of the composition, and wherein the spices have a particle size ranging from 0.050 to 0.900 mm;
   (iv) sterilized or pasteurized water in an amount from 80 to 99% by weight of the composition; and wherein the composition has a total calorie content from 0 to 100 based on 100 gram of the composition.

2. The composition according to claim 1 wherein the palate enhancing agent is a mixture of raspberries and pineapple in a weight ratio ranging from about 1:20 to about 20:1.

3. The composition according to claim 1 wherein caffeine is absent.

4. The composition according to claim 1 wherein water is present in an amount from 95 to 97.5% by weight of the composition.

5. The composition according to claim 1 wherein the cayenne pepper has a particle size ranging from 0.080 to 0.250 mm.

6. The composition according to claim 1 wherein the cayenne pepper has a particle size ranging from 0.149 to 0.210 mm.

7. A method for weight loss by a human, the human ingesting over a period of time repeated amounts of a beverage consisting essentially of:
   (i) cayenne pepper present in an amount from about 0.00001 to about 0.01% by weight of the composition, and wherein the cayenne pepper has a particle size ranging from 0.050 to 0.900 mm;
   (ii) a palate enhancing agent which is a fruit selected from the group consisting of pineapple, raspberry, lemon, grape, blueberry, cherry and mixtures thereof, the agent including pulp of the fruit, the palate enhancing agent being present in an amount from about 0.0001 to about 50% by weight of the composition;
   (iii) at least four spices which are black or white pepper, ginger, cinnamon and mustard seed each present in an amount from about 0.00001 to about 0.01% by weight of the composition, and wherein the spices have a particle size ranging from 0.050 to 0.900 mm;
   (iv) sterilized or pasteurized water in an amount from 80 to 99% by weight of the composition; and wherein the composition has a total calorie content from 0 to 100 based on 100 gram of the composition.

8. A beverage composition for weight loss consisting essentially of:

(i) cayenne pepper present in an amount from about 0.00001 to about 0.01% by weight of the composition, and wherein the cayenne pepper has a particle size ranging from 0.050 to 0.900 mm;
(ii) a palate enhancing agent which is a fruit selected from the group consisting of pineapple, raspberry, lemon, grape, blueberry, cherry and mixtures thereof, the agent including pulp of the fruit, the palate enhancing agent being present in an amount from about 0.0001 to about 50% by weight of the composition;
(iii) at least four spices which are black or white pepper, ginger, cinnamon and mustard seed each present in an amount from about 0.00001 to about 0.01% by weight of the composition, and wherein the spices have a particle size ranging from 0.050 to 0.900 mm;
(iv) sterilized or pasteurized water in an amount from 80 to 99% by weight of the composition; and wherein the composition has a total calorie content from 0 to 100 based on 100 gram of the composition; and
(v) milk thistle extract present in an amount from about 0.000001 to about 0.001.

9. A beverage composition for weight loss consisting essentially of:
(i) cayenne pepper present in an amount from about 0.00001 to about 0.01% by weight of the composition, and wherein the cayenne pepper has a particle size ranging from 0.050 to 0.900 mm;
(ii) a palate enhancing agent which is a fruit selected from the group consisting of pineapple, raspberry, lemon, grape, blueberry, cherry and mixtures thereof, the agent including pulp of the fruit, the palate enhancing agent being present in an amount from about 0.0001 to about 50% by weight of the composition;
(iii) at least four spices which are black or white pepper, ginger, cinnamon and mustard seed each present in an amount from about 0.00001 to about 0.01% by weight of the composition, and wherein the spices have a particle size ranging from 0.050 to 0.900 mm;
(iv) sterilized or pasteurized water in an amount from 80 to 99% by weight of the composition; and wherein the composition has a total calorie content from 0 to 100 based on 100 gram of the composition; and
(v) a vitamin B selected from the group consisting of $B_1$, $B_2$, $B_3$, $B_5$, $B_6$, $B_{12}$ and mixtures thereof present in an amount from about 0.000001 to about 0.001.

10. The composition according to claim 9 wherein the vitamin B is present as all of vitamins $B_1$, $B_2$, $B_3$, $B_5$, $B_6$ and $B_{12}$.

* * * * *